US006956381B2

(12) United States Patent
Dahan

(10) Patent No.: US 6,956,381 B2
(45) Date of Patent: Oct. 18, 2005

(54) FLEXIBLE PROBE FOR MEASURING MOISTURE CONTENT IN SOIL

(75) Inventor: Ofer Dahan, Midreshet Ben Gurion (IL)

(73) Assignee: The Board of Regents of University and Community College System of Nevada on Behalf of the Desert Research Institute, Reno, NV (US)

( * ) Notice: Subject to any disclaimer, the term of this patent is extended or adjusted under 35 U.S.C. 154(b) by 0 days.

(21) Appl. No.: 10/272,413

(22) Filed: Oct. 15, 2002

(65) Prior Publication Data

US 2003/0071637 A1 Apr. 17, 2003

Related U.S. Application Data

(60) Provisional application No. 60/329,794, filed on Oct. 12, 2001.

(51) Int. Cl.[7] .................. G01R 27/04; G01R 27/32; G01V 3/18
(52) U.S. Cl. ................... 324/643; 324/324
(58) Field of Search ............... 324/643, 637, 324/642, 324

(56) References Cited

U.S. PATENT DOCUMENTS

| | | | |
|---|---|---|---|
| 5,570,030 A | * 10/1996 | Wightman | 324/694 |
| 5,648,724 A | 7/1997 | Yankielun et al. | 324/533 |
| 5,726,578 A | 3/1998 | Hook | 324/643 |
| 5,801,537 A | 9/1998 | Siddiqui et al. | 324/643 |
| 5,954,450 A | * 9/1999 | Rolfe | 405/37 |
| 6,002,257 A | * 12/1999 | Thomas et al. | 324/324 |
| 6,078,181 A | 6/2000 | Robichaud et al. | 324/643 |
| 6,079,433 A | 6/2000 | Saarem | 137/1 |
| 6,100,700 A | 8/2000 | Yankielun et al. | 324/534 |
| 6,121,894 A | 9/2000 | Yankielun et al. | 340/870.13 |
| 6,441,622 B1 | 8/2002 | Wrzesinski et al. | 324/643 |
| 6,696,974 B1 | * 2/2004 | Mathis | 340/854.7 |

OTHER PUBLICATIONS

"Systems", FLUTE (Flexible Liner Underground Technologies, Ltd., Co.) Santa Fe, New Mexico, Internet Pages http://www.flut.com/sys_2.htm, Oct. 11, 2002, pp. 1–2.

Selker, John S., et al. "Noninvasive Time Domain Reflectometry Moisture Measurement Probe", Soil Sci. Soc. Am J., vol. 57, Jul.–Aug. 1993, pp. 934–936.

* cited by examiner

Primary Examiner—Anjan Deb
Assistant Examiner—John Teresinski
(74) Attorney, Agent, or Firm—Greenberg Traurig, LLC

(57) ABSTRACT

The embodiments of the invention are directed to a new apparatus and method of measuring the water content using time domain reflectometry (TDR), or electrical conductivity in deep soil levels to. The method uses flat, flexible, waveguides attached to a flexible sleeve filled with a filling material which press the flexible waveguides against an irregularly shaped interior borehole wall.

13 Claims, 4 Drawing Sheets

US 6,956,381 B2

FLEXIBLE PROBE FOR MEASURING MOISTURE CONTENT IN SOIL

CROSS REFERENCE TO RELATED APPLICATIONS

This application claims the benefit of U.S. Provisional Application No. 60/329,794, filed Oct. 12, 2001.

FIELD OF INVENTION

The embodiments of this invention relate to an apparatus and method for obtaining measurements of the dielectric constant or permittivity of soil in order to measure its water content.

BACKGROUND

Accurate determination of water content is an important aspect of most vadose zone monitoring programs. A common method for measuring soil water content in unsaturated soils is time domain reflectometry (TDR). In this method, the TDR technique involves the measurement of the propagation velocity of a high frequency signal transmitted along a probe. Since the dielectric constant of water (~80) is significantly higher than most soils (2–7), measurements of the velocity of propagation can be used to determine the soil volumetric water content. TDR probes are typically made with two or three metal rods that function as waveguides placed parallel to each other, inserted into the soil at the point where the measurements are to be made.

The use of TDR probes for measuring water content in natural undisturbed soil in the unsaturated zone between the land surface and the water table (the vadose zone) is often limited by the structure, depth and condition of the soil. In shallow soil, TDR probes inserted into the ground from the land surface create only minor disturbance of the natural soil properties. Inserting TDR probes into deep soil horizons can be problematic however, when a natural undisturbed soil condition is required. Standard TDR probes can be installed into deep levels, but this usually involves (1) excavating a deep trench followed by inserting the probes horizontally through the trench walls to the deeper soil horizons, or (2) drilling a wide diameter vertical borehole and using a special instrument to insert the TDR probe through the borehole wall into the surrounding soil.

Both the trench and wide diameter vertical borehole techniques are undesirable because they can significantly disturb the natural soil properties in the near-field environment where the TDR probes are installed. This disturbance may create preferential flow paths for water to bypass the natural soil material and affect the representativeness of the TDR reading. Even if the excavated trench or wide diameter borehole are backfilled, soil disturbances caused by those methods can create preferential flow paths for water and affect the representativeness of the TDR readings. When standard TDR probes are installed into undisturbed rocky or pebbly material, they are susceptible to bending, crimping or complete failure because they loose their parallel orientation. Deformation of the probes away from the parallel configuration can bias the readings and create uncertainties about the accuracy of the water content measurements. Stiff rods bearing TDR probes can be pushed into the ground under very high loads, but those rods are only built to be inserted into shallow layers and only work well in very soft soils.

Prior techniques have also used non-invasive TDR probes attached to the surface of the examined material. Those stiff acrylic pads bearing coiled waveguides allowed moisture measurements to be made only on relatively smooth and flat surfaces. These and other limitations of existing TDR probe installation techniques in the deep soils has led me to develop a new apparatus and method suitable for the measurement of the soil dielectric constant or permittivity and electrical conductivity in the deep vadose zone. The embodiments of the present invention allow multi level installation of soil moisture probes, which are based on dielectric constant or pemittivity measurements, to any desired depth from land surface with only minimal, if any, disturbance of the natural properties of the soil column.

SUMMARY

A first embodiment of the present invention is accomplished by using a flexible TDR probe. The flexible TDR probe is composed of flexible waveguides made of stainless steel attached to an outer side of a sleeve fabricated of a flexible material. The flexibility of the waveguides considerably improves their contact with borehole walls thereby increasing the reliability of desired measurements. The waveguides are attached to the exterior surface of the flexible sleeve which is sealed to prevent any leakage of the filling material from the sleeve into a borehole. The filling material generates outward pressure inside the flexible sleeve. The pressure forces the flexible waveguides against the borehole wall and improves the likelihood that the waveguides will have optimum contact with the borehole walls. The apparatus allows the flexible TDR probes or electrical conductivity probes to be installed along the sleeve length at the required spacing and desired depth. The apparatus may be used in both angled and vertically drilled boreholes.

LIST OF REFERENCE NUMERALS UTILIZED IN THE DRAWING

Figure 1:
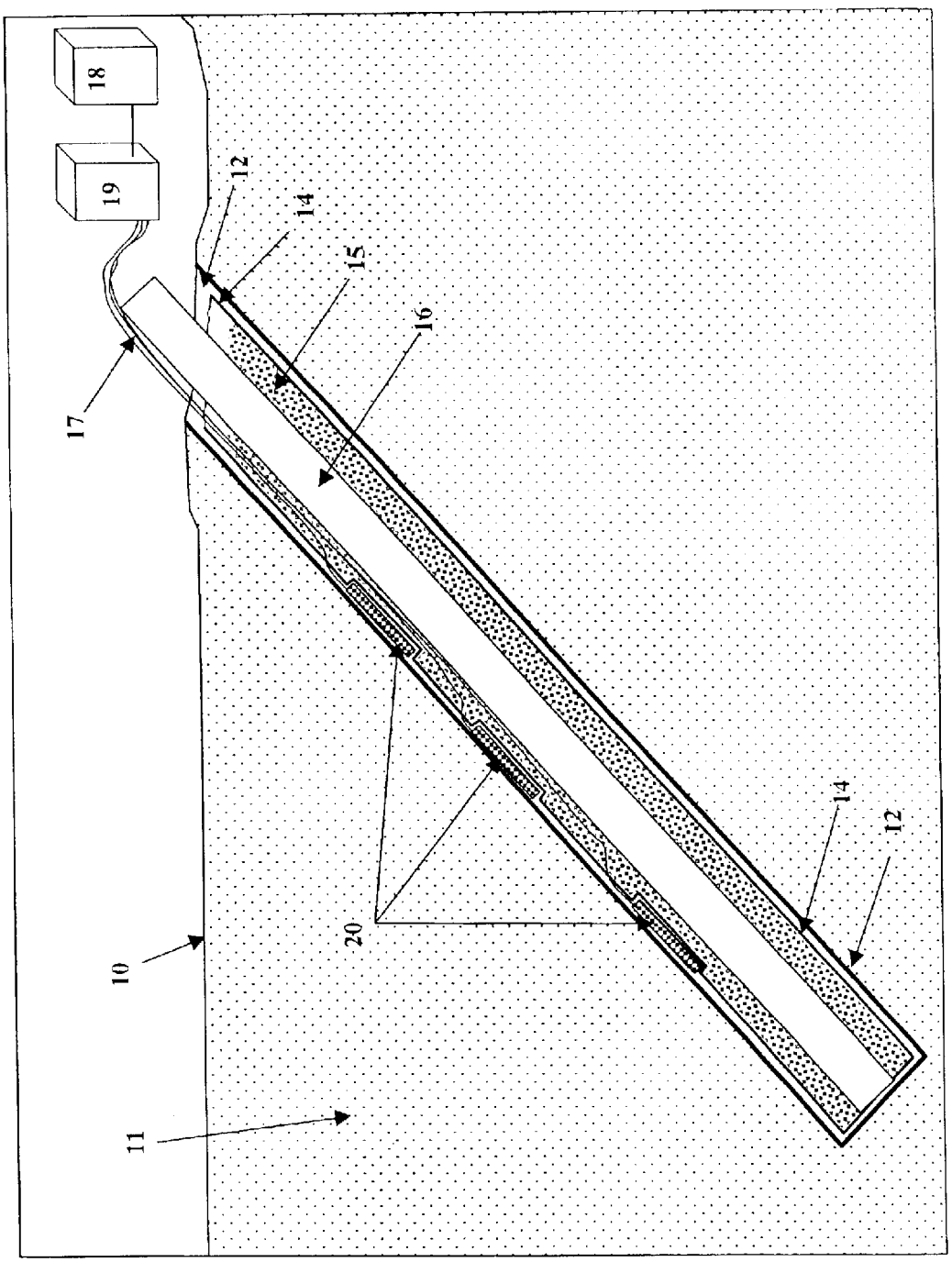
FIG. 1 is a cross sectional-side view of a first embodiment of the present invention showing placement of the apparatus with three flexible TDR probes into a slanted borehole through the soil.

10 land surface
11 soil
12 borehole
13-1 flexible waveguide
13-2 flexible waveguide
13-3 flexible waveguide
14 flexible sleeve
15 filling material
16 inner support
17 wires
18 data logger
19 cable tester
20 flexible TDR probe

DETAILED DESCRIPTION

In a first embodiment of the present invention, flexible TDR probes composed of flexible waveguides are attached to the outer surface of a flexible sleeve. The apparatus is placed into an angled borehole and the flexible sleeve is filled with a selected filling material which produces sufficient pressure to force the flexible waveguides up against a borehole wall so that water content or electrical conductivity of the soil can be measured.

Figure 2:
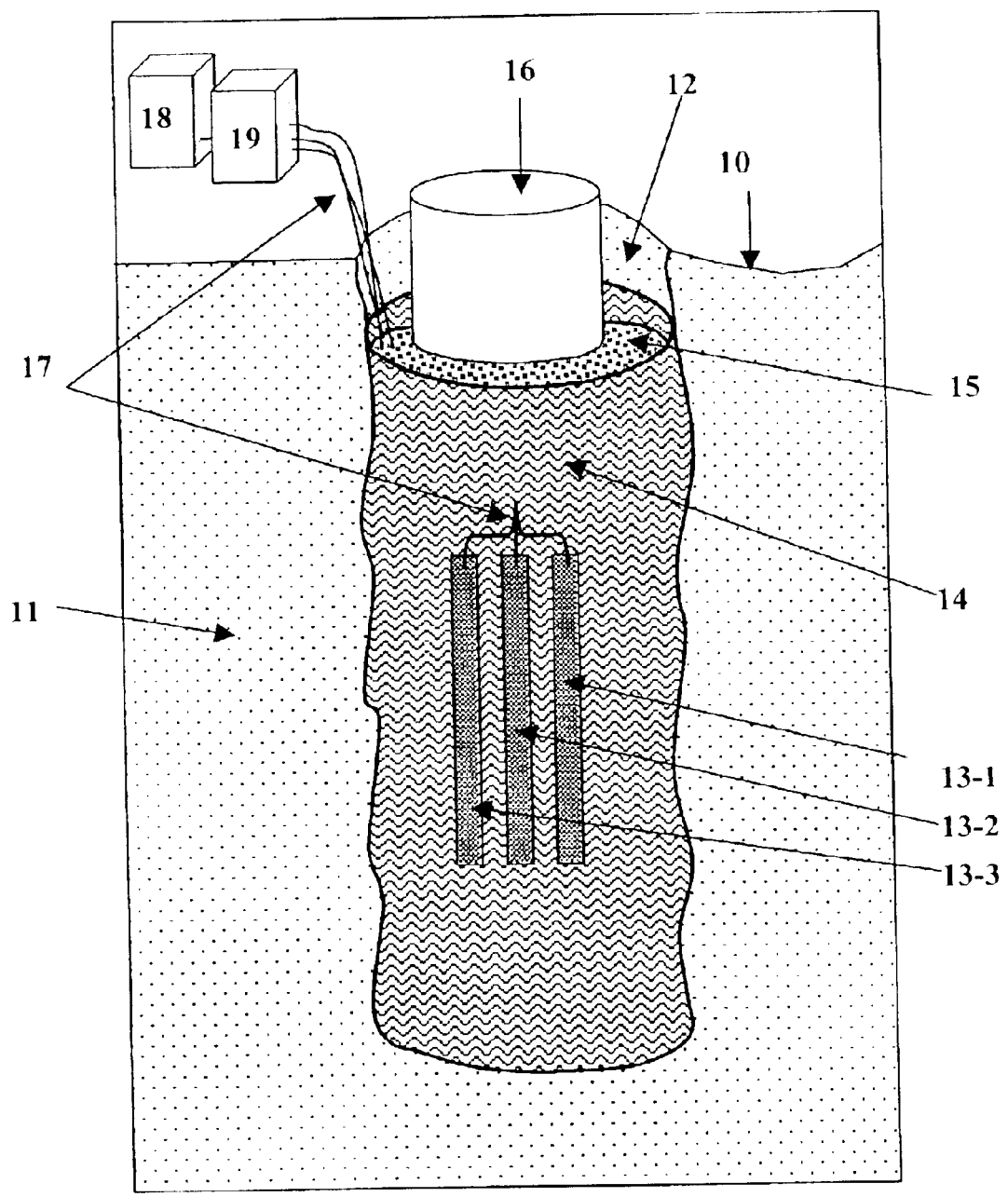
FIG. 2 is a cross sectional-front view of another embodiment of the present invention showing placement of the apparatus with a single flexible TDR probe composed of three flexible waveguides into a vertical borehole.
Figure 3:
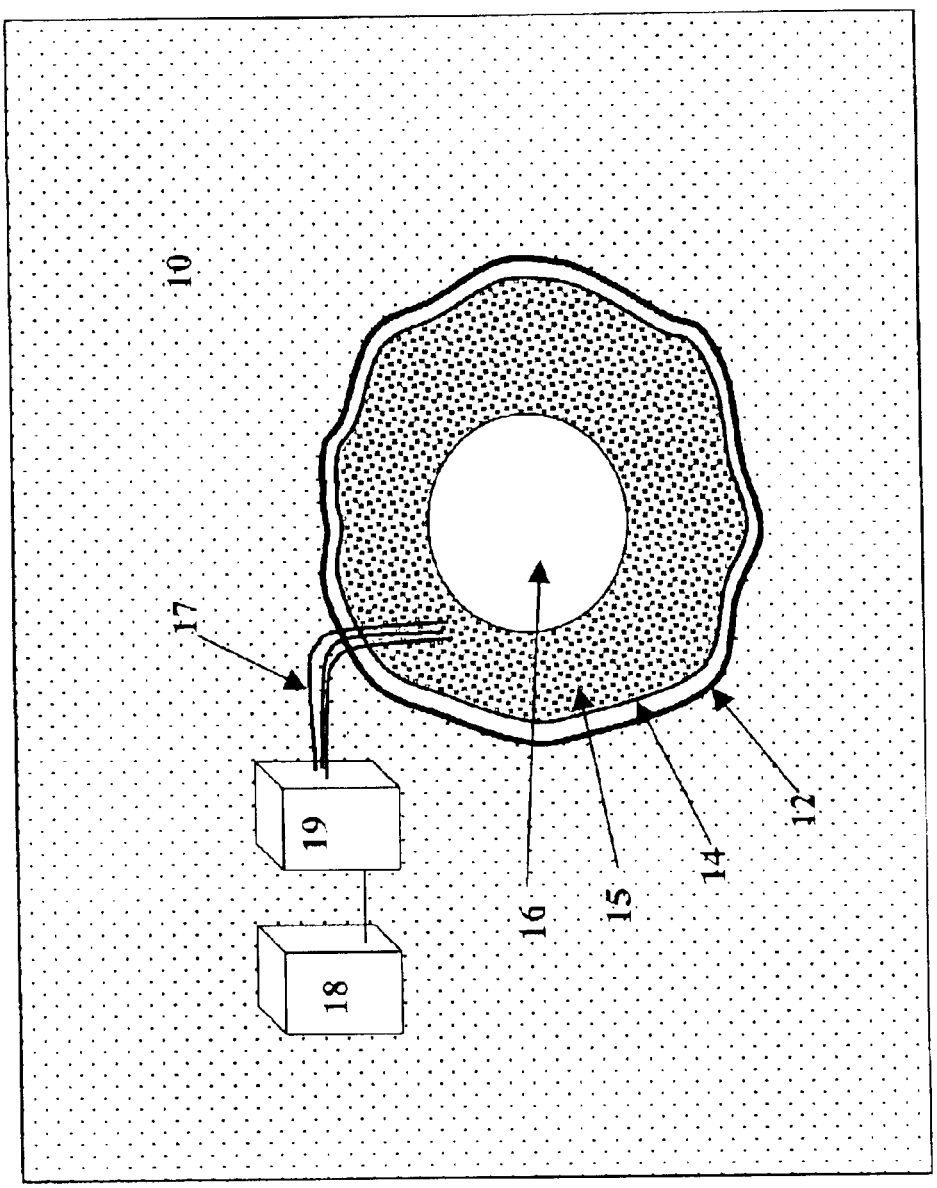
FIG. 3 is a top view of a first embodiment placed into a borehole.
Figure 4:
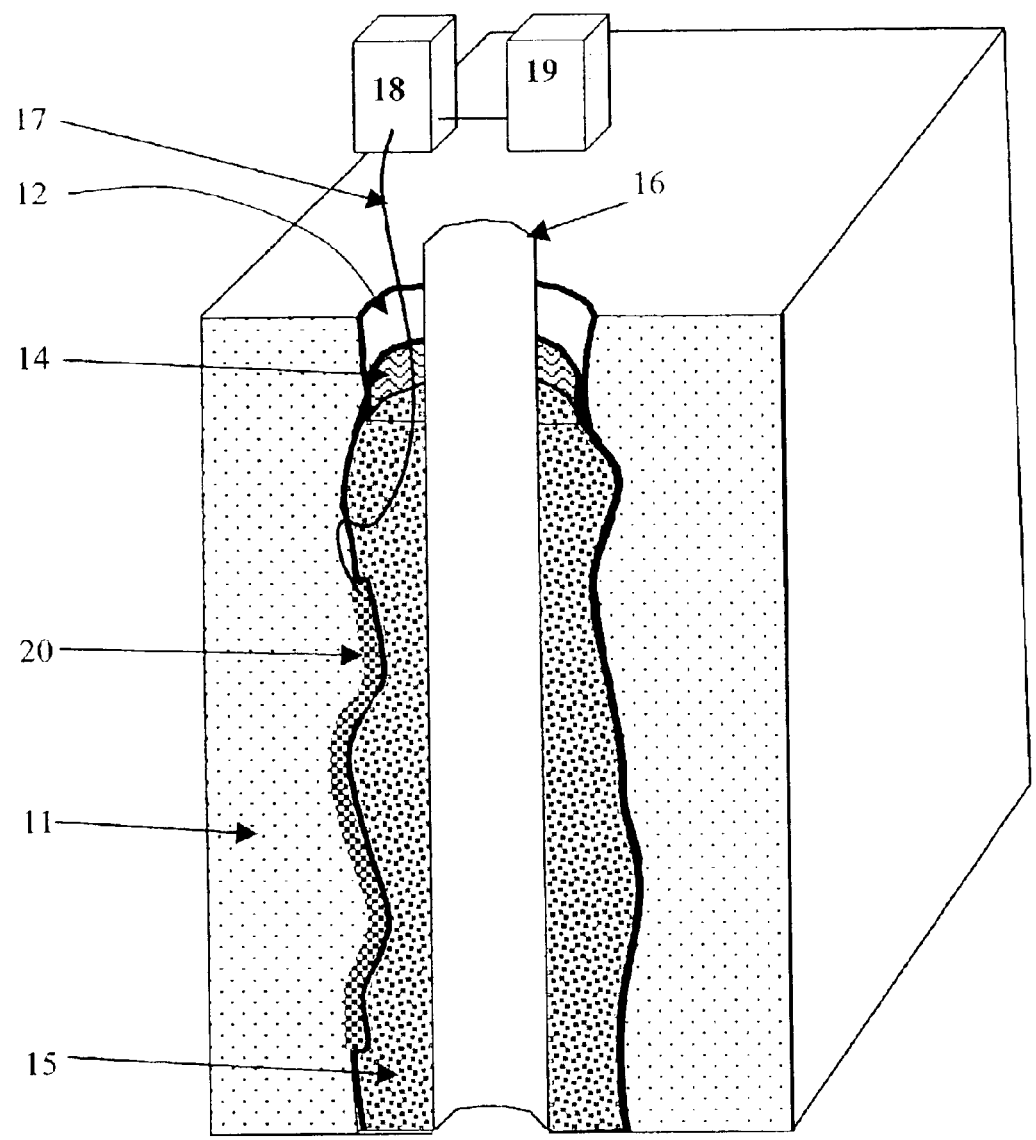
FIG. 4 is a diagrammatic perspective showing placement of a first embodiment of the present invention, containing a single flexible TDR probe, into a vertical borehole.

Referring now to the drawings wherein like characters refer to like elements throughout the various views and particularly to FIG. 2, which shows a first embodiment of the apparatus of the present invention.

Flexible waveguides 13-1 through 13-3 can be fabricated of any flat, flexible material capable of propagating an electronic current along its length. An example of a suitable flexible ribbon or band-like material for fabricating said waveguides 13-1 through 13-3 is stainless steel foil strips manufactured by Compac Industries. In an embodiment, the stainless steel foil strips forming the flexible waveguides 13-1 through 13-3 are sized 1.25 cm by 30 cm. Each waveguide 13-1 through 13-3 is attached to the flexible sleeve 14 in parallel to one another. While a first embodiment utilizes glue for attaching the waveguides 13-1 through 13-3, any adhesive means may be employed. Similar to a standard, three-rod TDR probe, each waveguide 13-1 through 13-3 is connected to a coaxial cable (not shown) and a center waveguide 13-2 is soldered to an inner conductor of the coaxial cable and the two outer waveguides 13-1 and 13-2 are soldered to the shield of the coaxial cable.

Each coaxial cable corresponding to each flexible TDR probe 20 is electrically connected, using electrical wires 17, to a cable tester 19 and a data logger 18. Said electrical wires 17 are run into a space between the sleeve 14 and an inner support 16 until they reach a point at which the flexible waveguides 13-1 through 13-3 are to be located. Said cable tester 19 is used for the measurement of a dielectric constant or permittivity of the soil. It is understood that, each flexible TDR probe 20 may be directly connected to its own electronic device that is capable of measuring the dielectric constant or permittivity of the soil. Other instruments commonly used for the purpose of Time Domain Reflectometry include Campbell Scientific TDR 100, Campbell Scientific CS505 and Trace, Decagon. In a first embodiment, three flexible waveguides 13-1 through 13-3 are attached to a flexible sleeve 14 to form a flexible TDR probe composed of three waveguides. A person skilled in the art will understand however, that the apparatus can be used with means for measuring the dielectric constant or permittivity, moisture content, or the electrical conductivity of said soil, and the number and placement of flexible probes 20 or waveguides 13-1 through 13-3 can vary.

As suggested above, in an alternative embodiment, an individual electronic device (not shown) (such as Campbell Scientific CS505, or Decagon ECH2O), which is capable of measuring the dielectric constant or permittivity of the soil, or a voltmeter can be wired directly to a set of flexible waveguides 13-1 through 13-3. Those skilled in the art understand that an alternative embodiment eliminates the need to use a cable tester.

A sleeve 14 can be fabricated from any flexible material able to be sufficiently sealed to retain the filling material 15 that is ultimately poured into a space between the sleeve 14 and an inner support 16. In a first embodiment, said flexible sleeve 14 is fabricated of 0.25 mm transparent flexible PVC liner, but any flexible material including vinyl, rubber, or other sealable fabric capable of preventing leakage of the filling material 15 from the sleeve 14 and into a borehole 12 and flexible enough to allow the waveguides 13-1 to 13-3 to conform to the shape and irregularities of the borehole 12 wall, is suitable. The sleeve 14 should be fabricated so that once the filling material 15 has been added, and the sleeve 14 is in its expanded state, its exterior diameter is slightly larger than the borehole 12 wall. In this manner, the sleeve 14 can adapt to the irregularities and diameter variations of the borehole 12. The length of the sleeve 14 is fabricated to length generally equal to or longer than the length of the borehole, but a shorter sleeve 14 may be fabricated. In another embodiment, the sleeve 14 is a closed flexible container capable of maintaining a pressure.

The inner support 16, as best seen in FIG. 1, is placed into the sleeve 14. While any type of material having the physical ability to support the sleeve 14 during its installation into the borehole 12 is suitable for the embodiments of the present invention, PVC pipe is ideal because it provides the rigidity necessary for installation of the apparatus into the borehole 12. Moreover, the volume of the sleeve 14 is reduced by the volume of the inner support 16. Reducing the volume of the sleeve 14 reduces the amount of filling material 15 necessary to expand the sleeve 14 to the circumference of the borehole 12. In an alternative embodiment the inner support is eliminated.

Once the sleeve 13 is inserted into the soil, a liquid filling material 15 is poured into a space between the sleeve 14 and the inner support 16. A two-component liquid urethane (not shown) is one example of filling material 15. Said filling material 15 creates a hydrostatic pressure in the sleeve 14 which causes the sleeve 14 to expand and force the flexible waveguides 13-1 through 13-3, which are affixed to the exterior of the sleeve 14, against any irregularly shaped borehole 12 wall. Other types of resin, for example, epoxy, or polyester, or concrete may be used but any liquid which consolidates after being poured into the sleeve 14, and has sufficient density to expand the sleeve 14 against the borehole 12 wall thereby pressing the flexible waveguides 13-1 through 13-3 against the borehole 12 wall is suitable. If retrieval of the waveguides 13 and the apparatus from the soil is required after measurements are taken, then a liquid or pressurized gas filling material can be used. Once the apparatus is placed into a borehole 12, which has been drilled to a desired depth of soil 11, filling material 15 is then placed into the space between the interior portion of the sleeve 14 and the inner support 16. The filling material is allowed to expand and harden so that the expanded sleeve 14 fills the borehole 12 pressing the flexible waveguides 13-1 through 13-3 against the internal diameter of the borehole 12.

Method of Use

For the sake of brevity, the first embodiment of the present invention will be used to describe a method of use. However, alternative embodiments may require alternative techniques. Using standard techniques for a chosen material, a flexible sleeve 14 is fabricated with a diameter slightly larger then an estimated maximum borehole 12 diameter. A flexible TDR probe 20, composed of flexible waveguides 13-1 through 13-3, are glued along the length of the flexible sleeve 14 at the desired spacing and to the desired depth and are electrically connected to the cable tester 19 and the data logger 18. A PVC pipe 16 is then placed inside the sleeve 14 for rigidity. Ideally, the integrity of the sleeve 14 is pressure tested using compressed air to ensure that no filling material 15 will leak from the sleeve 14 into the annular space of the borehole 12.

A pressure tested assembly, best shown in FIG. 1, is inserted into the borehole 12, with flexible TDR probes 20 aligned along an upper part of the borehole 12. The space between the inner support 16 and the flexible sleeve 14 is then filled with a filling material 15 composed of a two-part low viscosity liquid urethane 15. As the liquid urethane is poured into the sleeve 14, it generates hydrostatic pressure such that the sleeve 14 expands to fill the irregularly shaped borehole 12 wall. The flexible waveguides 13-1 through 13-3 of each flexible TDR probe 20, are forced against the borehole 12 wall, and then fixed in their position once the urethane filling material 15 fully cures. The desired measurements are then read at the cable tester 19 and the data logger 18. In an alternative embodiment, filling material 15 could include sand or compressed gas. In an alternative embodiment, the borehole 12 can be drilled to the depth of groundwater and the inner PVC pipe may be used for sampling groundwater and for measuring water table fluctuations. A thermocouple may be placed next to each flexible waveguide 13-1 through 13-3 and provide information regarding water flow.

While in accordance with the provisions of the Patent Statutes the preferred forms and embodiment of the invention have been illustrated and described, it will be apparent to those of ordinary skill in the art that various changes and modifications may be made without deviating from the inventive concept set forth above.

I claim:

1. A method of use of an apparatus used to measure soil parameters, comprising;
   providing a flexible container having a closed first end, an open end, and a sidewall defining an interior volume adapted to contain a material;
   affixing one or more electrical conductors, to said flexible container, said one or more conductors being substantially flexible;
   electrically coupling said one or more conductors to a means for measuring said soil parameters;
   placing said container and said one or more conductors into a hole in said soil;
   injecting said container with a liquid such that an outer surface of said one or more electrical contacts, contacts said soil; and
   monitoring said soil parameters from said soil.

2. The method of claim 1 wherein said second end of said container open.

3. The method of claim 1 wherein said second end is closed.

4. The method of claim 1 wherein said second end is substantially sealed.

5. The method of claim 4 wherein said second end contains a means for accepting a liquid.

6. The method of claim 1 wherein said material is a liquid.

7. The method of claim 1 wherein said liquid is a resin.

8. The method of claim 1 wherein said interior volume of said container is adapted to receive an article for reducing said interior volume.

9. The method of claim 1 wherein said reduced interior volume of said container is adapted to contain a liquid.

10. The method of claim 1 wherein said parameter is moisture content.

11. The method of claim 1 wherein said parameter is a electrical conductivity.

12. The method of claim 1 wherein said parameters is a dielectric.

13. The method of claim 1 wherein said one or more electrical conductors is substantially flat.

* * * * *